United States Patent [19]

Miller

[11] Patent Number: 4,751,296

[45] Date of Patent: Jun. 14, 1988

[54] PROCESS FOR 4-HALOMETHYL-AZETIDINONES BY CYCLIZATION OF O-ACYLHYDROXAMATES

[75] Inventor: Marvin J. Miller, South Bend, Ind.

[73] Assignee: University of Notre Dame du Lac, Notre Dame, Ind.

[21] Appl. No.: 893,748

[22] Filed: Aug. 6, 1986

[51] Int. Cl.⁴ .................. C07D 205/08; C07D 403/04; C07D 413/04; C07B 39/00

[52] U.S. Cl. .................................. 540/355; 558/263; 260/500.5 H

[58] Field of Search ........................................ 540/355

[56] References Cited

U.S. PATENT DOCUMENTS 4,174,316  11/1979  Christensen et al. ........... 260/239 A

OTHER PUBLICATIONS

Rajendra, G., and Miller, M. J., Tetrahedron Letters, vol. 26, No. 44, pp. 5385–5388, 1985.
Biloski, A. J. et al., J. Amer. Chem. Soc., 1982, 104, 3233.
Huffman, W. F., J. Amer. Chem. Soc., 1977, 99:7, pp. 2352–2353.
Bryan, D. Bolen, et al., J. Amer. Chem. Soc., 1977, 99:7, pp. 2353–2355.
Salzmann, T. N., J. Amer. Chem. Soc., 1980, 102, pp. 6161–6163.
Afzali-Ardakani, A. and Rapoport, H., J. Org. Chem., 45, 4817–4820, (1980).
Miller, M. J. et al., J. Org. Chem., 1982, 47, 4928–2933.
Mattingly, P. G. et al., J. Org. Chem., 1980, 45, 410–415.

*Primary Examiner*—Mark L. Berch
*Attorney, Agent, or Firm*—William B. Scanlon; Leroy Whitaker

[57] ABSTRACT

A process for 4-halomethylazetidin-2-ones is provided which comprises mixing in an inert solvent a positive halogen reagent in the presence of a weak base with a $\beta,\gamma$-unsaturated O-acylhydroxamate of the formula

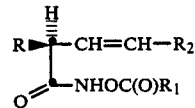

wherein R is protected amino, lower alkyl or phenyl substituted lower alkyl, $R_2$ is a substituent such as lower alkyl which may be substituted by formyl, hydroxy, halogen, etc., and $R_1$ is alkoxy, benzyloxy, etc. When R is a protected amino group, the process provides cis-4-halomethylazetidin-2-ones, while when R is alkyl or phenylalkyl, the trans isomer is obtained. The 4-halomethylazetidinones are useful intermediates for known antibiotic compounds.

16 Claims, No Drawings

PROCESS FOR 4-HALOMETHYL-AZETIDINONES BY CYCLIZATION OF O-ACYLHYDROXAMATES

The invention described herein was made in the course of work under a grant or award from the Department of Health and Human Services.

BACKGROUND OF THE INVENTION

This invention relates to a process for preparing substituted azetidinones. In particular, it relates to a process for preparing 3$\beta$-substituted-amino -4$\beta$-halomethyl-1-hydroxyazetidin-2-ones and 3$\beta$-alkyl -4$\alpha$-halomethyl-1-hydroxyazetidin-2-ones.

Azetidinones substituted in the 4-position by halomethyl are useful intermediates for nuclear analogs of penicillins and cephalosporins, carbapenems, as well as functionalized monocyclic $\beta$-lactams. For example, such azetidinones are disclosed by Huffman, W. F., et al., J. Amer. Chem. Soc., 1977, 99, 2352; Salzmann, T. N., et al., J. Amer. Chem. Soc., 1980, 102, 6161; and by Miller, M. J., et al., J. Org. Chem., 1982, 47, 4928. Although synthetic routes to the 4-halomethylazetidinones are known, such routes usually require multi-step elaboration of the 4-halomethyl group after the $\beta$-lactam ring has been formed. Because of the importance of substituted azetidinones as intermediates for a variety of $\beta$-lactam antibiotics, a more efficient and direct route to these intermediates having the desired stereochemistry would be highly useful.

SUMMARY $\beta,\gamma$-Unsaturated O-acyl hydroxamates are cyclized directly to 4-halomethyl-1-acyloxyazetidin-2-ones in a process comprising the oxidative cyclization with positive halogen in the presence of a weak base. $\alpha$-Alkyl-$\beta$,E-unsaturated 0-acylhydroxamates provide trans-3-alkyl-4-halomethylazetidin-2-ones, while $\alpha$-protected amino-$\beta,\gamma$-unsaturated 0-acylhydroxamates obtained with amino acids afford cis-3$\beta$-protected amino 4$\beta$-halomethylazetidin -2-ones. For example, 2-(benzyloxycarbonylamino) but-3-eneoic acid benzyloxycarbonyloxyamide is treated in aqueous acetonitrile with bromine and potassium carbonate to provide 1-benzyloxycarbonyloxy-3$\beta$-(benzyloxycarbonylamino)-4$\beta$-bromomethylazetidin-2-one as the predominant product.

The azetidinones are useful intermediates for monocyclic $\beta$-lactam, carbapenam, carbapenem, carbacepham, and carbacephem antibiotics.

DETAILED DESCRIPTION

According to the process of this invention, a $\beta,\gamma$-unsaturated 0-acylhydroxamate represented by the formula 1

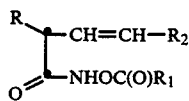

wherein
R is lower alkyl, lower alkyl substituted by phenyl, or protected amino;
R$_1$ is C$_1$-C$_6$ alkyl, C$_1$-C$_6$ alkoxy, phenyl, phenoxy, benzyloxy and said phenyl, phenoxy and benzyloxy substituted by lower alkyl, lower alkoxy, halogen or nitro;
R$_2$ is hydrogen, lower alkyl, $-(CH_2-)_m$CHO; $-(CH_2-)_n$O-R$_2'$, $-(CH_2-)_p$X', $-(CH_2-)_q$COOR$_2''$ or a vinyl group represented by the formula $-CH=CH-R_3$ wherein R$_2'$ and R$_2''$ are, respectively, a hydroxy-protecting group and a carboxy-protecting group, X' is chloro, bromo or iodo, m, n, p and q each represent 0, 1 or 2 and R$_3$ is hydrogen, lower alkyl, -COOR$_2''$ wherein R$_2''$ is as defined above, phenyl, m(C$_1$-C$_4$ alkoxy)phenyl or furyl; is mixed in an inert solvent with a positive halogen reagent in the presence of a weak base to provide, when R is a protected amino group, a cis-azetidinone represented by the formula 2

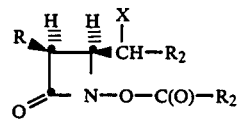

and when R is other than protected amino, a trans-azetidinone represented by the formula 3

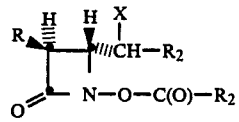

wherein R, R$_1$ and R$_2$ the same meanings as defined above and X is chloro, bromo or iodo.

The process is carried out at a temperature between about $-20°$ C. and about 45° C. and preferably at about 0° C. to about 25° C.

The term "positive halogen reagent" refers to those substances generally recognized as affording X+ electrophilic halogen. A wide variety of halogenating agents which can be used in the practice of the invention are known to those skilled in the art as sources of positive halogen. Representative of suitable positive halogen reagents are the halogens, chlorine, bromine and iodine, sulfuryl chloride, sulfuryl bromide, the arylseleno halides such as phenylseleno chloride, the hypohalites such as sodium hypochlorite, calcium hypochlorite and sodium hypobromite, N-haloamides and N-haloimides such as N-chlorosuccinimide, N-bromosuccinimide, and N-chlorophthalimide, the N-halohydantoins such as the N,N'-dibromohydantoins, the N-halosaccharins such as N-chlorosaccharin, and the acyl hypohalites such as acetyl hypochlorite, butyryl hypochlorite, acetyl hypobromite and propionyl hypobromite.

The oxidative cyclization process is carried out in the presence of a "weak base". The term "weak base" as used herein refers to inorganic and organic bases having a pK$_a$ of between about 6 and about 11 and preferably between about 7 and about 10. A large number of such weak bases are known and are exemplified by those listed in the Handbook of Biochemistry and Molecular Biology, Vol. 1, 3rd ed., G. D. Fassman, CRC Press, 1976, pp. 305–347. The base may be soluble or insoluble in water. Water soluble weak bases such as the alkali metal carbonates are used in the process with a water miscible solvent containing from about 3% to about 10% by volume of water. Suitable weak bases include the alkali metal carbonates such as lithium carbonate, sodium carbonate and potassium carbonate, tertiary amines such as the trialkylamines, e.g., triethylamine, tripropylamine and tributylamine, benzyldiethylamine, pyridine, quinoline, N-methylmorpholine, and the like. Dilute aqueous sodium hydroxide or potassium hydroxide may also be used, e.g., dilute aqueous sodium hydroxide at a concentration of about 1–2%.

Water miscible solvents suitable for use in the process with a water soluble base are those inert to the positive halogen reagent and include the common solvents such as the lower alcohols, methyl alcohol, ethyl alcohol and propyl alcohol, the water miscible polyhydric alcohols such as ethylene glycol and propylene glycol, nitriles such as acetonitrile and propionitrile, and ethers such as tetrahydrofuran and amides such as dimethylformamide and dimethylacetamide. For use in the process, the water miscible solvent contains between about 3% and about 10% by volume of water. A preferred solvent is acetonitrile containing from about 5% to 10% water.

Water insoluble bases may be used with any inert solvent in which the base is at least partially soluble. Preferably, the base is completely soluble in the inert solvent.

Inert solvents for use in the process are any of the commonly used organic solvents such as the water miscible solvents noted above and water immiscible solvents such as methylene chloride, chloroform, dichloroethane, and ethyl acetate. Inert solvents are those which do not react with either the $\beta,\gamma$-unsaturated O-acylhydroxamate or the positive halogen reagent.

The process is best carried out at a temperature between about 0° C. and about 25° C. by using a slight excess of the weak base, i.e., in excess of equimolar with respect to the starting material 1, and an amount of positive halogen reagent slightly in excess of equimolar.

The process is performed as follows: the $\beta,\gamma$-unsaturated O-acylhydroxamate 1 is dissolved in the inert solvent and the solution is cooled to a temperature between about −5° C. and about 25° C. The weak base is added and if it is a water soluble base insoluble in the solvent, water is added. The mixture is agitated vigorously and the positive halogen reagent is added with continued vigorous agitation during and after addition. The positive halogen reagent is preferably added as a solution of the reagent in the inert solvent.

The process of the invention proceeds rapidly and on a laboratory scale is completed in about 15 minutes or less. When carried out on a larger scale, e.g., manufacturing scale, somewhat longer times may be required in that addition, cooling and the mixing of reagents require more time.

The 4-halomethyl azetidinone is recovered from the reaction mixture and is separated from minor side products by conventional means. For example, the reaction mixture is mixed with a water immiscible organic solvent such as ethyl acetate, and the organic layer is washed with water and a reducing agent such as sodium sulfite to neutralize any excess halogen present. After drying, the solvent is evaporated and the residue containing the product is chromatographed, e.g., over silica gel. The cis-azetidinone 2 generally can be separated from the minor products on the chromatogram by changing the polarity of the eluting mixture, the cis isomer 2 is generally eluted with the less polar eluting mixture, while the minor product is eluted with eluting mixtures of increased polarity. A useful eluting mixture for the chromatographic separation is ethyl acetatehexane. Other mixtures of polar and nonpolar solvents may be used.

The process of this invention wherein an $\alpha$-protected amino-$\beta,\gamma$-unsaturated O-acylhydroxamate is cyclized (formula 1, R=protected amino) surprisingly provides the azetidinone-2-one 2 in the cis form in high yields. The minor side product in this instance appears to be the isomeric trans-4-halomethylazetidinone, although other products are possible. In contrast, when the group R of the starting material 1 is other than a protected amino group, e.g., ethyl or benzyl, the product is almost exclusively the trans-4-halomethylazetidinone 3.

A preferred embodiment of the process comprises the oxidative cyclization of an $\alpha$-protected amino-$\beta,\gamma$-unsaturated O-acylhydroxamate (formula 1, R=protected amino) to a 3$\beta$-protected amino-4$\beta$-halomethylazetidin-2-one (formula 2). Preferred conditions for this embodiment comprise the use of an alkali metal carbonate, especially potassium carbonate, as the weak base, chlorine or bromine as the positive halogen reagent and acetonitrile containing between about 5% and about 10% by volume of water. Preferably, the cyclization is carried out at a temperature between about 0° C. and about 10° C.

In a further preferred embodiment, the positive halogen reagent is bromine. Other positive halogen reagents that may be noted are the hypohalites such as sodium or potassium hypochlorite, calcium hypochlorite and sodium hypobromite.

Preferred O-acyl groups of the hydroxamate 1 are represented when $R_1$ is $C_1$–$C_6$ alkyl, benzyloxy or a substituted benzyloxy group. For example, the acetoxy group $R_1$=methyl and the benzyloxycarbonyloxy group $R_1$=benzyloxy are preferred. The benzyloxycarbonyloxy group is especially preferred in that it provides versatility in subsequent synthetic steps, since it can be removed by either hydrolysis or hydrogenolysis.

The terms employed in the definition of the starting material 1 and the azetidinone products 2 and 3 have the following meanings. "Lower alkyl" refers to the $C_1$–$C_4$ straight chain alkyl groups, excepting t-butyl, such as methyl, ethyl, and n-propyl; "lower alkyl substituted by phenyl" refers to benzyl, 1-phenethyl, 2-phenethyl, 3-phenylpropyl, and the like; "$C_1$–$C_6$ alkoxy" refers to methoxy, ethoxy, propoxy, n-butoxy, t-butoxy, pentoxy, and the like; phenyl, phenoxy, and benzyloxy substituted by lower alkyl, lower alkoxy, halogen or nitro, are exemplified by the mono-or di-lower alkyl, lower alkoxy or nitro-substituted groups such as 4-methylphenyl, 2,4-diethylphenyl, 4-methoxyphenyl, 4-ethoxyphenyl, 3,4-dimethoxyphenyl, 4-nitrophenyl, 4-isopropylphenoxy, 3-methoxyphenoxy, 3,4-diethoxyphenoxy, 3-nitrophenoxy, 4-nitrophenoxy, 3,4-dimethylbenzyloxy, 4-nitrobenzyloxy, 2,6-dimethoxybenzyloxy, 4-t-butyloxybenzyloxy and the mono or polyhalo groups such as 4-chlorophenyl, 3-bromophenyl, 2,4-dichlorobenzyl, 3,5-dichlorophenoxy, 4-fluorophenoxy, pentachlorophenoxy, 4-bromobenzyloxy, 3,5-dichlorobenzyloxy and like substituted groups.

The term "protected amino" refers to the substituted amino group represented by the formula R'—O—C-(O)— wherein R' is $C_1C_6$ alkyl, halo-substituted $C_{1-C6}$ alkyl, $C_2$–$C_6$ alkenyl, $C_3$–$C_7$ cycloalkyl, isobornyl, adamantyl, benzyl or diphenylmethyl and said benzyl or diphenylmethyl group mono- or di-substituted by $C_1$–$C_{10}$ alkyl, $C_1$–$C_4$ alkoxy, nitro or halogen.

The proctecting group of he protected amino group R of formulae 1, 2 and 3 can be a $C_1$–$C_6$ alkoxycarbonyl group such as methoxycarbonyl, ethoxycarbonyl, t-butyloxycarbonyl, isobutyloxycarbonyl, and the like; a halo-substituted $C_1$–$C_6$ alkoxycarbonyl group such as trichloroethoxycarbonyl, tribromoethoxycarbonyl, 2-iodotrichloroethoxycarbonyl, 2,2,3-trichlorobutoxycarbonyl, and the like; a $C_2$–$C_6$ alkenyloxycarbonyl group such as allyloxycarbonyl, 2-butenyloxycarbonyl, 3-hexenyloxycarbonyl, and the like; a $C_3$–$C_7$ cycloalkyloxycarbonyl group such as cyclopropyloxycarbonyl, cyclopentyloxycarbonyl, cyclohexyloxycarbonyl, and the like; isobornyloxycarbonyl, adamantyloxycarbonyl, a benzyloxycarbonyl group or a substituted benzyloxycarbonyl group wherein the phenyl ring is substituted by nitro, chloro, bromo, $C_1$–$C_4$ alkoxy or $C_1$–$C_{10}$ alkyl; or the diphenylmethoxycarbonyl group which can be similarly substituted.

Examples of O-acyl groups

of the formulae 1, 2 and 3 are acetyl, propionyl, butyryl valeryl, and the like; benzoyl or benzoyl substituted by halogen, $C_1$–$C_4$ alkoxy, $C_1$–$C_4$ alkyl or nitro; a $C_1$–$C_4$ alkoxycarbonyl group such as methoxycarbonyl, ethoxycarbonyl and t-butoxycarbonyl; benzyloxycarbonyl or a substituted benzyloxycarbonyl group substituted on the phenyl group by nitro, $C_1$–$C_4$ alkoxy, halogen or $C_1$–$C_4$ alkyl such as p-nitrobenzyloxycarbonyl; phenoxycarbonyl or a substituted phenoxycarbonyl group substituted by halogen, $C_1$–$C_4$ alkoxy, $C_1$–$C_4$ alkyl or nitro, such as 4-chlorophenoxycarbonyl, pentachlorophenoxycarbonyl, 4-bromophenoxycarbonyl, 4-nitrophenoxycarbonyl, and like acyl groups.

Examples of the 4-halomethylazetidin-2-ones provided by the process described herein are contained in the following table wherein R, $R_1$, $R_2$ and X refer to formulae 2 and 3.

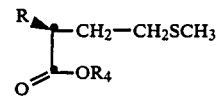

to the corresponding sulfoxide with an oxidizing agent such as sodium periodate. The sulfoxide is thermally degraded to the β, γ-unsaturated ester by heating at a temperature of about 180° C. to about 190° C. as shown below.

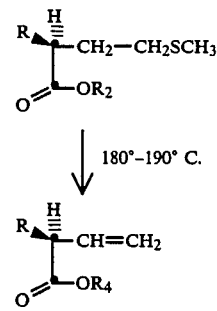

The procedure is a modification of the procedure of Rapoport, H., et al., *J. Org. Chem.*, 45, 4817 (1980).

The $R_4$ ester group is removed by hydrolysis and the unsaturated acid is reesterified with an easily displaceable ester group such as one formed with N-hydroxysuccinimide, N-hydroxyphthalimide or N-hydroxybenztriazole. The displaceable ester is reacted with hydroxylamine to provide the corresponding hydroxamic acid represented by the formula

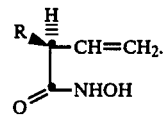

| R | $R_1$ | $R_2$ | X |
|---|---|---|---|
| $C_6H_5CH_2OC(O)NH-$ | $C_6H_5CH_2O-$ | H | Br |
| $C_6H_5CH_2OC(O)NH-$ | $C_6H_5CH_2O-$ | $CH_3$ | Br |
| $C_6H_5CH_2OC(O)NH-$ | $C_6H_5CH_2O-$ | H | Cl |
| $C_2H_5OC(O)NH-$ | $CH_3$ | H | Br |
| $CCl_3CH_2OC(O)NH-$ | $C_2H_5O$ | $-CHO$ | Br |
| $CCl_3CH_2OC(O)NH-$ | cyclopentyloxy | $-COOC_2H_5$ | Br |
| cyclopentyloxycarbonylamino | pentachlorophenoxy | $-COOC_2H_5$ | Cl |
| $C_2H_5$ | $CH_3$ | H | Br |
| $C_2H_5$ | 4-nitrobenzyloxy | CHO | I |
| $t-C_4H_9OC(O)NH$ | $C_6H_5$ | $-CH_2COOC_2H_5$ | Br |
| $C_6H_5CH_2OC(O)NH-$ | $CH_3$ | $-CH=CHCH_3$ | Br |
| $C_6H_5CH_2OC(O)NH-$ | $CH_3$ | $-CH=CHCOOC_2H_5$ | Cl |
| $C_6H_5CH_2OC(O)NH-$ | $C_6H_5CH_2O$ | $-CH=CH-C_6H_5$ | Br |
| $t-C_4H_9OC(O)NH$ | $-n-C_3H_7$ | $-CH=CH-\underset{OCH_3}{C_6H_4}$ | Br |
| $C_6H_5CH_2-$ | $C_6H_5$ | $C_2H_5$ | Cl |

The α-(protected amino)-β,γ-unsaturated O-acylhydroxamates 1 (R=Protected amino) used as the starting materials in the process are obtained by known methods. One such method comprises the conversion of an amino-protected L-methionine ester represented by the formula The hydroxamic acid is then acylated with an acid anhydride, e.g., acetic anhydride or benzoic acid anhydride, or with an alkyl haloformate, a benzyl haloformate, a phenyl haloformate or substituted phenyl haloformate such as ethyl chloroformate, isobutyl chloroformate, phenyl chloroformate, pentachlorophenyl chloroformate or benzyl chloroformate, to provide 1.

The 3β-(protected amino)-4β-halomethyl-1-acyloxyazetidin -2-one (formula 2) or the trans azetidinone-ones (formula 3) formed in the process is converted by known procedures to the corresponding 1-hydroxyazetidinone represented by the following formulae.

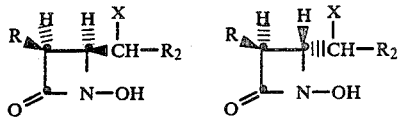

For example, an O-alkanoyl substituted 2 such as O-acetyl is removed under mild hydrolysis conditions, while the benzyloxycarbonyl and phenoxycarbonyl type O-acyl groups are removed by hydrogenolysis over a palladium catalyst such as 5% Pd-C.

The 1-hydroxy group can be removed by reduction with titanium trichloride by the procedure described by Miller et al., *J. Org. Chem.*, 1980, 45, 410 to provide the 1-unsubstituted 3β-(protected amino)-4β-halomethylazetidin -2-one. The latter azetidinones and the 1-hydroxy precursors thereof are useful intermediates for the preparation of nuclear analogs of penicillins and cephalosporins, carbapenems and also functionalized monocyclic β-lactam antibiotics, see e.g., Miller, et al., *J. Org. Chem.*, 47, 4928 (1982). The following Preparations and Examples further describe the process of the invention.

PREPARATION 1

Cbz Vinylglycine, $CH_2=CH-CH(NHCbz)COOH$

A. L-Methionine methyl ester

L-Methionine (50.0 g, 0.335 mole) was suspended in 350 ml of anhydrous methyl alcohol and the suspension was cooled to 0° C. Thionyl chloride (28.2 ml, 0.38 mole, 1.1 eq) was added dropwise with stirring to the suspension over 1 hour, and the clear solution was stirred for 14 hours at room temperature. The solution was evaporated on a rotary evaporator to remove about 200 ml of methyl alcohol and 400 ml of diethyl ether was added to the concentrate. The mixture was stored in the refrigerator for 4 hours and the white crystalline L-methionine methyl ester hydrochloride salt was filtered. A second crop of the ester hydrochloride was obtained from the filtrate. The total yield of product was 67.0 g.

NMR: ($D_2O$) δ2.06 (s, 3H), 2.1–2.46 (m, 2H), 2.46–2.83 (m, 2H), 3.86 (s, 3H), 4.23–4.46 (t, 1H).
IR : 3300–2400 (v. broad), 2000, 1743 $cm^{-1}$.

B. Cbz protected L-methionine methyl ester

The L-methionine methyl ester hydrochloride prepared as described in A above (45.0 g, 0.225 mole) and used without further purification was dissolved in 350 ml of water and the pH of the solution was adjusted to 7.0 with 4N sodium hydroxide. Sodium bicarbonate (66.2 g, 0.788 mole, 3.5 eq) was added cautiously with stirring to the solution followed by 37.2 ml of neat benzyl chloroformate (0.2475 mole, 1.1 eq) and the white suspension was stirred at room temperature overnight. The reaction mixture was extracted ten times with 100 ml portions of ethyl acetate and the extracts were combined, washed twice with 100 ml portions of water, four times with 50 ml portions of 5% hydrochloric acid, twice with 100 ml portions of brine, were dried over magnesium sulfate, filtered and evaporated in a rotary evaporator yielding 70.2 g of the Cbz protected L-methionine methyl ester. The product was contaminated with some benzyl alcohol and benzyl chloroformate.

NMR: ($DCCl_3$/TMS) δ2.03 (s, 3H), 1.83–2.33 (m, 2H), 2.33–2.63 (m, 2H), 3.72 (s, 3H), 4.33–4.63 (m, 1H), 5.1 (s, 2H), 5.4–5.67 (br d, 1H), 7.4 (s, 5H).
IR : 3400 br, 1745 (shoulder) and 1720 $cm^{-1}$.

C. Cbz protected L-methionine methyl ester sulfoxide

The crude product of B above (70 g, 0.225 mole) was dissolved in 500 ml of methyl alcohol and the clear solution was cooled to 0° C. A solution of 51.1 g of sodium periodate in 500 ml of water was added dropwise with stirring to the solution over 1.5 hours. A white precipitate of periodate started to form within a few minutes, and the reaction mixture was allowed to warm to room temperature over 10 hours with continual stirring. The precipitate was filtered and washed with 100 ml of methyl alcohol. The filtrate was evaporated to a low volume and the aqueous concentrate was saturated with sodium chloride and then extracted 10 times with 75 ml portions of ethyl acetate. The extracts were combined, washed twice with 50 ml portions of water, twice with 100 ml portions of brine, dried over magnesium sulfate and evaporated to give the product as an oil. Volatile impurities were removed from the oil by heating to 100° C. with stirring under vacuum (0.1 mm). There were obtained 59.93 g of partially pure product as a reddish brown viscous oil.

NMR: ($CDCl_3$) δ2.00–2.5 (m, 2H), 2.53 (s, 3H), 2.56–2.90 (m, 2H), 3.75 (s, 3H), 4.26–4.6 (m, 1H), 5.1 (s, 2H), 6.23–6.83 (br d, 1H), 7.38 (s, 5H).
IR : 3250 br, 1730 (shoulder), 1720 $cm^{-1}$.

D. Cbz protected vinylglycine methyl ester

The methionine sulfoxide methyl ester product obtained above in C (crude) (6.38 mmole) was heated with vigorous stirring in a 10 ml flask at a temperature of 180° C. to 190° C. for 1.5 to 2 hours. The progress of the reaction was monitored by thin layer chromatography. When the starting material had completely disappeared (tlc), the oil was allowed to cool to room temperature. There were obtained 1.4 g of the impure vinylglycine ester product as a reddish brown oil.

The NMR spectrum of the oil indicated the presence of about 10 –15% of the α,β unsaturated isomer.

NMR crude: ($CDCl_3$) δ3.70 (s, 3H), 4.76–5.03 (br m, 1H), 5.03–5.5 (m, 4H), 5.6–6.3 (m, 2H), 7.35 (s, 1H).
IR: 3250 br, 1735 $cm^{-1}$.

E. Cbz protected vinylglycine

The crude product from D (1.4 g) was dissolved in 50 ml of 1:1 5% HCl:glacial acetic acid, and the solution was heated at the reflux temperature for 50–70 minutes. After the vinylglycine methyl ester had reacted, as shown by thin layer chromatography, the mixture was allowed to cool to room temperature. The mixture was evaporated to remove the acetic acid and the aqueous residue was saturated with sodium chloride and then extracted 5 times with 50 ml portions of ethyl acetate. The extracts were combined, dried over magnesium sulfate and evaporated in vacuo to an oil. The oil chromatographed on silica using ethyl acetate-hexanes (10% to 30%). The fractions containing the product were evaporated and the product was crystallized from ethyl acetate-hexanes to yield 0.77 g of the product Cbz protected vinylglycine as very pale yellow flakes melting at about 119° C.to about 121° C.

NMR: δ4.8–5.33 (m, 5H), 5.53–6.17 (m, 2H), 7.35 (s, 5H), 10.5 (br 1H).

IR : 3600–2400 v. br., 1725 cm$^{-1}$.

PREPARATION 2

Cbz protected vinylglycine N-(benzyloxycarbonyloxy) amide

A. Cbz protected vinylglycine N-hydroxysuccinimido ester

The Cbz protected vinylglycine prepared as described by Preparation 1 (0.7 g, 2.98 mmole) was dissolved in 30 ml of dry methylene chloride and the solution was cooled to 0° C. While the solution was maintained in a dry atmosphere, N-hydroxysuccinimide (0.388 g, 3.27 mmole) was added followed by a solution of dicyclohexylcarbodiimide (DCC) (0.7368 g, 3.57 mmole) in 10 ml of dry methylene chloride. The DCC solution was added over 30 minutes. The reaction mixture was allowed to warm to room temperature and was stirred for 4 hours. The precipitate of dicyclohexylurea was filtered and the filtrate was diluted with 200 ml of ethyl acetate. The diluted mixture was washed twice with 30 ml portions of water, once with 50 ml of brine and was dried and evaporated in vacuo to a residual oil. The oil was dissolved in 10 ml of benzene and filtered to remove remaining dicyclohexylurea. The benzene was evaporated from the filtrate, the oil redissolved in benzene and the solution filtered again to remove more urea. The filtrate was evaporated to give 1.06 g of the succinimido ester as a very pale yellow oil contaminated with about 5% dicyclohexylurea (NMR).

B. Cbz protected vinylglycine N-hydroxyamide

The impure succinimido ester prepared above in A (1.06 g, 2.98 mmole) was added to a solution of hydroxylamine hydrochloride (0.62 g, 8.93 mmole) in 50 ml of a 1:1 mixture of THF:water. Next, sodium carbonate (1.5 g, 17.85 mmole) was added and the reaction mixture was stirred at room temperature for about 4 hours. When the succinimido ester had all reacted as shown by thin layer chromatography, the reaction mixture was diluted with 250 ml of ethyl acetate. The mixture was washed three times with 30 ml portions of 2% hydrochloric acid, twice with 25 ml of water, three times with 25 ml portions of brine and was dried and evaporated. There were obtained 0.58 g of the impure N-hydroxyamide derivative as a slightly brownish yellow oil.

NMR: (CDCl$_3$) δ4.67–6.33 (br m, 7H), 7.30 (s, 5H), 8–9 (br 1H).

IR : 3650–2500 v. br., 1690, 1625 (shoulder) cm$^{-1}$.

The N-hydroxyamide product obtained (0.58 g, 2.32 mmole based on 100% purity) was dissolved in 25 ml of acetonitrile immediately after its preparation and the solution was cooled to 0° C. Pyridine (0.2 ml, 2.43 mmole) was added with stirring followed by benzyl chloroformate (0.35 ml, 2.32 mmole). The reaction mixture was stirred at 0° C.for one hour and was then diluted with 150 ml of ethyl acetate. The solution was washed with water, 2% hydrochloric acid and brine, was dried and evaporated to give 0.63 g of the N-benzyloxycarbonyloxy derivative as white crystals after crystallization of the residue from methylene chloride-hexanes. The product was contaminated with about 5% of dicyclohexylurea.

NMR: (CDCl$_3$) δ4.75–6.4 (overlapping m, 7H), 7.35 (d, 10H).

EXAMPLE 1

1-Benzyloxycarbonyloxy-3β-benzyloxycarbonylamino-4β-bromomethylazetidin-2-one

The Cbz protected vinylglycine derivative prepared as described by Preparation 2 above (0.40 g, 1.04 mmole) was dissolved in 40 ml of acetonitrile and the solution was cooled to about 4° C. Potassium carbonate (0.151 g, 1.09 mmole) was added to the solution followed by 2.5 ml of water. The mixture was stirred vigorously for one minute after addition and then a solution of 58.7 μl (1.14 mmole) of bromine in 12 ml of acetonitrile was added dropwise. The reaction mixture stirred vigorously for 5 minutes and slowly for 2 minutes and was then diluted with 200 ml of ethyl acetate. The mixture was washed with water, 30 ml of a 10% solution of sodium sulfite and with brine, was dried and evaporated in vacuo to an oil. The oil was chromatographed on silica using ethyl acetate-hexanes (8 to 25%) to give two fractions. The first fraction contained the pure cis isomer of the product as represented by the formula

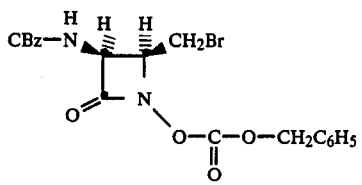

The cis isomer was obtained crystalline from methylene chloride-hexanes: 0.186 g of white crystals.

(300 MHz, CDCl$_3$) δ3.35–3.6 (m, 2H), 4.45–4.58 (m, 1H), 5.15 (s, 2H), 5.1 –5.25 (m, overlapping the singlet, 1H), 5.27 (s, 2H), 5.75–5.87 (br. d, 1H), 7.3–7.45 (d, 10H).

IR : 1818, 1790, 1725 cm$^{-1}$.

The second fraction gave 0.172 g of a colorless oil which was a mixture of the cis isomer (above) and a minor amount of what appeared to be the trans isomer.

EXAMPLE 2

1-Benzyloxycarbonyloxy-3β-benzyl-4α-bromomethylazetidin -2-one

A. 2-Benzylbut-3-eneoic acid (1.1 g, 6.24 mmole) was added to a dry flask equipped with a septum and a magnetic stirring bar and the flask was cooled to 0° C. with an ice bath. Oxalyl chloride (0.59 ml, 6.86 mmole) was added neat to the flask and the ice bath was removed. The mixture was stirred at room temperature for 8 hours to provide the acid chloride as a yellow oil.

NMR (CDCl$_3$/TMS): δ2.76–3.07 (m, 2H), 3.23–3.9 (q, 1H), 5.06–5.43 (m, 2H), 5.63–6.10 (m, 1H), 7.28 (s, 1H).

B. A solution of hydroxylamine hydrochloride (0.455 g, 6.55 mmole) in 25 ml of absolute methyl alcohol and a solution of potassium hydroxide (0.85 g, 12.8 mmole) in 25 ml of absolute methyl alcohol were cooled to 0° C. and mixed together. A solution of 2-benzylbut-3-eneoic acid chloride, prepared as described in A above, in 10 ml of dry THF was added at 0° C. to the mixed solutions with stirring. The cooling bath was removed and the mixture was stirred at room temperature for 20 minutes. The pH of the mixture was adjusted to 4.0 with 5% hydrochloric acid and the mixture was evaporated to remove methyl alcohol. The aqueous concentrate was saturated with sodium chloride and extracted four times with 75 ml portions of ethyl acetate. The extracts were combined, washed with brine, dried over magnesium sulfate, filtered and evaporated to dryness. The 2-benzylbut-3-eneoic acid N-hydroxamide obtained as a pale brownish yellow oil was used without further purification in the following step.

C. The crude N-hydroxamide (ca. 6.24 mmole) obtained in B above was dissolved in 25 ml of acetonitrile to form a 0.25M solution and the solution was cooled to 0° C. Pyridine (0.53 ml, 6.55 mmole) was added to the cold solution with stirring followed by 1.03 ml of benzyl chloroformate (6.87 mmole) which was added neat. The mixture was stirred for one hour with gradual warming to room temperature. The mixture was diluted with 200 ml of ethyl acetate and the solution was washed twice with 30 ml portions of water, twice with 25 ml portions of 10% aqueous citric acid and with 50 ml of brine and was dried over magnesium sulfate. The drying agent was filtered and the filtrate evaporated to yield 2.1 g of the N-benzyloxycarbonyloxy amide as a yellow oil. The product was purified by chromatography on silica gel using 5% to 15% ethyl acetate-hexane to yield 1.12 g of purified N-benzyloxycarbonyloxy-2-benzylbut-3-eneoic acid amide represented by the formula

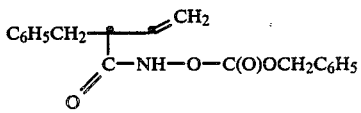

NMR(CDCl$_3$-TMS): δ2.73–3.30 (m, 3H), 4.96–5.5 (m, 4H), 5.63–6.10 (m, 1H), 7.0–7.6 (m, 10H), 9.3 (br, 1H).

IR: 3700–2400 cm$^{-1}$ (v. br), 1800–1680 cmhu −11640 cm$^{-1}$ (shoulder).

D. The hydroxyamate C (0.2053 g, 0.6 mmole) was dissolved in 10 ml of acetonitrile and 87 mg (0.66 mole) of potassium carbonate was added followed by 2 ml of water. The mixture was stirred vigorously for one minute at room temperature and a solution of 0.69 mmole of bromine in 5 ml of acetonitrile was added dropwise over 2.5 minutes with very vigorous stirring. The mixture was stirred for one minute post addition, diluted with 150 ml of ethyl acetate and the solution washed twice with 25 ml portions of water, with 25 ml of 10% aqueous sodium bisulfite, with 30 ml of brine, was dried and filtered. The solvent was evaporated from the dried solution and the residue containing the title compound was chromatographed on silica using from 20% to 40% ethyl acetate-hexane. There was obtained 0.196 g of pure (+,−) title compound, represented by the following formula, as a colorless oil in 77% yield.

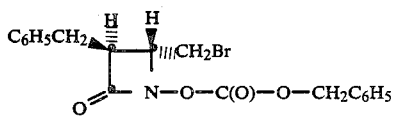

NMR (300 MHz, CDCl$_3$): δ2.96–3.10 (m, 1H), 3.15–3.3 (m, 2H), 3.33–3.55 (ddd, 2H), 4.07 4.19 (m, 1H), 5.3 (s, 2H), 7.2–7.53 (m, 10H).

IR: 1810, 1785 cm$^{-1}$.

EXAMPLE 3

1-Benzyloxycarbonyloxy-4-bromomethylazetidinone

To a solution of 0.3 g (1.28 mmole) of N-benzyloxycarbonyloxy but-3-eneoic acid amide in 20 ml of acetonitrile was added 0.1857 g (1.36 mmole) of potassium carbonate followed by 2 ml of water. The mixture was stirred vigorously for one minute and a solution of 0.2383 g (1.34 mmole) of N-bromosuccinimide in 5 ml of acetonitrile was added dropwise over 5 minutes with continued vigorous stirring. Stirring was continued for 10 minutes post addition and then the mixture was diluted with 200 ml of ethyl acetate. The solution was washed with water, aqueous 10% sodium bisulfite and brine and was dried over magnesium sulfate. The solvent was evaporated to provide 0.4686 g of the title compound as a pale yellow oil. The product was contaminated with minor amounts of succinimide and N-hydroxy-4-bromomethylazetidinone.

EXAMPLE 4

N-Benzyloxycarbonyloxy-4-(2-bromopropyl)azetidinone

A. N-Benzyloxycarbonyloxy-trans-hex-3-eneoic acid amide trans-Hex-3-eneoic acid (10.0 g, 87.61 mmole) was converted to the hydroxamic acid via 1) formation of the acid chloride with oxalyl chloride and 2) reaction of the acid chloride with hydroxylamine hydrochloride at 0° C. in methyl alcohol in the presence of excess 85% potassium hydroxide in methyl alcohol.

The crude hydroxamic acid (uncrystallized) was dissolved in 150 ml of dry tetrahydrofuran and the solution cooled to 0° C. Pyridine (7.44 ml, 92 mmole) was added with stirring to the cold solution and after 5 minutes benzyloxycarbonyl chloride (13.1 ml, 87.6 mmole, 95% pure) was added. The reaction mixture was stirred at 0° C. for 40 minutes and then was diluted with 300 ml of ethyl acetate and 150 ml of hexane. The solution was washed twice with 50 ml portions of water, twice with 50 ml portions of 1N HCl, again with 50 ml of water and with 50 ml of brine and was dried over magnesium sulfite. Evaporation of the solvents provided the N-benzyloxycarbonyloxy amide as a solid residue. The product was crystallized from ethyl acetate-hexane in 3 crops while cooling the solution from room temperature to 0° C. The first crop was crystalline white product (18.35 g, 76.6% yield) while the second and third crops were pale yellow.

The N-benzyloxycarbonyloxy trans-hex-3-eneoic acid amide (0.3168 g, 1.20 mmole) was dissolved in 20 ml of acetonitrile and the solution cooled to 0° C. Potassium carbonate (0.1696 g, 1.23 mmole) was added followed by 7 ml of water. During the additions the solution was stirred vigorously and for one minute after. Next, a solution of bromine in 5 ml of acetonitrile was added dropwise over 4 minutes with vigorous stirring. After stirring was continued for one minute, the solution was diluted with 150 ml of ethyl acetate and was washed with 25 ml of water, 30 ml of 10% aqueous sodium bisulfite and with 30 ml of brine. The solution was dried, filtered and evaporated to yield the title compound as a pale yellow oil. The oil was chromatographed on silica using from 10% to 40.1% ethyl acetate-hexane. There were obtained 0.217 g (52.8 % yield)

of the product represented by the following formula as a pale yellow oil.

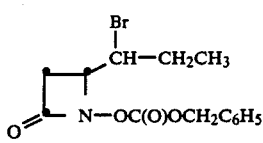

I claim:

1. A process for preparing a 4-halomethylazetidin-2-one of the formula

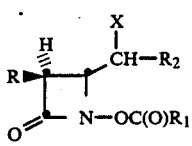

which comprises mixing in an inert solvent β, γ-unsaturated O-acylhydroxamate of the formula

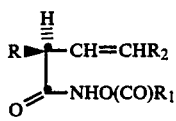

in the presence of a weak base with a positive halogen reagent, wherein

R is protected amino, lower alkyl or lower alkyl substituted by phenyl;

$R_1$ is $C_1$-$C_6$ alkyl, $C_1$-$C_6$ alkoxy, phenyl, phenoxy, benzyloxy and said phenyl, phenoxy and benzyloxy substituted by lower alkyl, lower alkoxy, halogen or nitro;

$R_2$ is hydrogen, lower alkyl,—$(CH_2)_m$CHO, —$(CH_2)_n$OR$_2'$, —$(CH_2)_p$X', —$(CH_2)_q$CO$_2$R$_2''$, or a —CH=CH—R$_3$, wherein R$_2'$ and R$_2''$ are, respectively, a hydroxy-protecting group and a carboxy-protecting group, X' is chloro, bromo or iodo, m, n, p and q each are 0, 1 or 2, and R$_3$ is hydrogen, lower alkyl, —CO$_2$R$_2''$, phenyl, m(C$_1$-C$_4$ alkoxy)-phenyl or furyl; and X is chloro, bromo or iodo; provided that, when R is a protected amino group, the 4-halomethylazetidinone is a cis- 3,4-disubstituted azetidinone of the formula

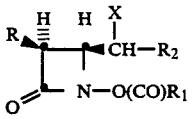

and when R is other than protected amino, the 4-halomethylazetidinone is a trans-3,4-disubstituted azetidinone of the formula

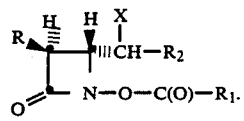

2. The process of claim 1 wherein R is a protected amino group.

3. The process for preparing a cis-4-bromomethylazetidin-2-one of the formula

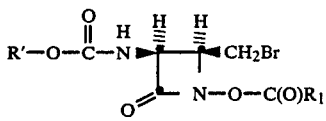

wherein R' is benzyl or substituted benzyl and $R_1$ is benzyloxy or substituted benzyloxy; which comprises mixing in an inert solvent a β, γ-unsaturated O-acylhydroxamate of the formula

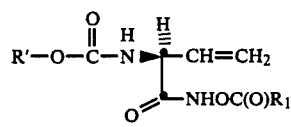

wherein R' and $R_1$ 2 have the same meanings as defined above, with bromine in the presence of a weak base.

4. The process of claim 1 wherein X is bromo.

5. The process of claim 1 wherein R is other than protected amino.

6. The process of claim 2 wherein R is a group of the formula R'—O—C(O)— wherein R' is $C_1$-$C_6$ alkyl, halo-substituted $C_1$-$C_6$ alkyl, $C_2$-$C_6$ alkenyl, $C_3$-$C_7$ cycloalkyl, isobornyl, adamantyl, benzyl, diphenylmethyl or said benzyl and diphenylmethyl mono- or disubstituted by $C_1$-$C_{10}$ alkyl, $C_1$-$C_4$ alkoxy, nitro or halogen or R is phthalimido or 4,5-diphenyloxazol-4-ene-2-one-3-yl.

7. The process of claim 2 wherein $R_2$ is hydrogen or lower alkyl.

8. The process of claim 2 wherein X is bromo.

9. The process of claim 2 wherein $R_1$ is benzyloxy or substituted benzyloxy.

10. The process of claim 5 wherein R is ethyl or benzyl.

11. The process of claim 10 wherein X is bromo.

12. The process of claim 11 wherein R is benzyl and $R_1$ is benzyloxy or substituted benzyloxy.

13. The process of claim 3 wherein the weak base is an alkali metal carbamate.

14. The process of claim 13 whrein the solvent is acetonitrile containing between about 5% and about 10% by volume of water.

15. The process of claim 14 wherein the temperature is between about 0° C. and about 10° C.

16. The process of claim 13 wherein the alkali metal carbonate is potassium carbonate.

* * * * *